United States Patent [19]

Malfer

[11] Patent Number: 4,997,456
[45] Date of Patent: Mar. 5, 1991

[54] FUEL COMPOSITIONS

[75] Inventor: Dennis J. Malfer, Crestwood, Mo.

[73] Assignee: Ethyl Petroleum Additives, Inc., St. Louis, Mo.

[21] Appl. No.: 405,222

[22] Filed: Sep. 11, 1989

[51] Int. Cl.$^5$ ................................................ C10L 1/22
[52] U.S. Cl. ...................................... 44/347; 548/545
[58] Field of Search .................... 44/63, 62, 71, 72, 73, 44/57

[56] References Cited

U.S. PATENT DOCUMENTS

| | | | |
|---|---|---|---|
| 3,806,456 | 4/1974 | Vogel | 44/63 |
| 3,847,561 | 11/1974 | Feldman | 44/63 |
| 3,897,351 | 7/1975 | Davis et al. | 252/34 |
| 4,098,585 | 7/1978 | Vartanian | 44/63 |
| 4,198,306 | 4/1980 | Lewis | 44/63 |
| 4,203,730 | 5/1980 | Hanson | 44/63 |
| 4,240,803 | 12/1980 | Andress, Jr. | 44/63 |
| 4,652,273 | 3/1987 | Maldonado et al. | 44/63 |
| 4,780,111 | 10/1988 | Dorer et al. | 44/63 |

Primary Examiner—Margaret B. Medley
Attorney, Agent, or Firm—John F. Sieberth

[57] ABSTRACT

Detergent additives for reducing or preventing deposits in the carburetor or in injectors are described. They are produced by reacting (a) at least one mono- or polycarboxylic acylating agent containing an average of from about 12 to about 50 carbon atoms in the molecule and having an acyclic aliphatic group containing an average of at least 12 but less than 30 carbon atoms, with (b) at least one alkanol polyamine containing an average of at least 4 carbon atoms. Succinimides made from 2-(2-aminoethylamino)ethanol have proved especially effective in reducing carburetor deposits.

38 Claims, No Drawings

FUEL COMPOSITIONS

TECHNICAL FIELD

This invention relates to fuel compositions for internal combustion engines. More particularly it relates to fuel compositions containing ashless dispersant-detergents capable of reducing and/or preventing the deposit of solid materials in internal combustion engines and in particular in the fuel intake systems and/or related engine parts.

BACKGROUND

The prior art discloses many ashless dispersants useful as additives in fuels and lubricant compositions. A large number of such ashless dispersants are derivatives of high molecular weight carboxylic acid acylating agents. Typically, the acylating agents are prepared by reacting an olefin (e.g., a polyalkene such as polybutene) or a derivative thereof, containing for example at least 30 to 50 aliphatic carbon atoms, with an unsaturated carboxylic acid or derivative thereof such as acrylic acid, methacrylic acid, maleic acid, fumaric acid and maleic anhydride. Dispersants are prepared from the high molecular weight carboxylic acid acylating agents by reaction with, for example, amines characterized by the presence within their structure of at least one N-H group, alcohols, reactive metal or reactive metal compounds, and combinations of the above. U.S. Pat. No. 4,234,435 summarizes some of the prior art relative to the preparation of such carboxylic acid derivatives.

It also has been suggested that the carboxylic acid derivative compositions such as those described above can be post-treated with various reagents to modify and improve the properties of the compositions. Acylated nitrogen compositions prepared by reacting the acylating reagents described above with an amine can be post-treated, for example, by contacting the acylated nitrogen compositions thus formed with one or more post-treated reagents selected from the group consisting of boron oxide, boron oxide hydrate, boron halides, boron acids, esters of boron acid, carbon disulfide, sulfur, sulfur chlorides, alkenyl cyanides, carboxylic acid acylating agents, aldehydes, ketones, phosphoric acid, epoxides, etc. Lists of the prior art relating to post-treatment of carboxylic ester and amine dispersants with reagents such as those described above are contained in a variety of patents such as U.S. Pat. No. 4,203,855 (Col. 19, lines 16-34) and U.S. Pat. No. 4,234,435 (Col. 42, lines 33-46).

U.S. Pat. No. 3,216,936 describes lubricant additives which are compositions derived from the acylating of alkylene polyamines. More specifically, the compositions are obtained by reaction of an alkylene amine with an acidic mixture consisting of a hydrocarbon-substituted succinic acid having at least about 50 aliphatic carbon atoms in the hydrocarbon group and an aliphatic monocarboxylic acid, and thereafter removing the water formed by the reaction. The ratio of equivalents of said succinic acid to the mono-carboxylic acid in the acidic mixture is from about 1:0.1 to about 1:1. The aliphatic mono-carboxylic acids contemplated for use include saturated and unsaturated acids such as acetic acid, dodecanoic acid, oleic acid, naphthenic acid, formic acid, etc. Acids having 12 or more aliphatic carbon atoms, particularly stearic acid and oleic acid, are especially useful. The products described in the '936 patent also are useful in oil-fuel mixtures for two-cycle internal combustion engines.

British Pat. No. 1,162,436 describes ashless dispersants useful in lubricating compositions and fuels. The compositions are prepared by reacting certain specified alkenyl substituted succinimides or succinic amides with a hydrocarbon-substituted succinic acid or anhydride. The arithmetic mean of the chain lengths of the two hydrocarbon substituents is greater than 50 carbon atoms. Formamides of monoalkenyl succinimides are described in U.S. Pat. No. 3,185,704. The formamides are reported to be useful as additives in lubricating oils and fuels.

U.S. Pat. Nos. 3,639,242 and 3,708,522 describe compositions prepared by post-treating mono- and polycarboxylic acid esters with mono- or polycarboxylic acid acylating agents. The compositions thus obtained are reported to be useful as dispersants in lubricants and fuels.

U.S. Pat. No. 4,780,111 describes fuel compositions containing a hydrocarbon-soluble dispersant prepared generally by the post-treatment of a nitrogen-containing composition with mono- and polycarboxylic acids which may be aliphatic or aromatic carboxylic acids, preferably the latter. The nitrogen-containing compositions which are post-treated in accordance with U.S. Pat. No. 4,780,111 are obtained by reacting an acylating agent with alkylene polyamines or alkanol amines. The patent reports that when such fuel compositions are utilized in internal combustion engines, and in particular, fuel-injected internal combustion engines, the amount of solid deposits on the various parts of the internal combustion engines ar reduced.

Use of such post-treatment procedures adds to the complexity of the production process and to the cost of the product so formed.

THE INVENTION

This invention provides novel fuel compositions and additives therefor which require no post-treatment procedures such as described for example in U.S. Pat. No. 4,780,111. Moreover, the resulting fuel compositions have been found highly effective in reducing or preventing carburetor or injector deposit formation or build up in internal combustion engines.

In accordance with one of its embodiments this invention provides a fuel composition comprising a major amount of a liquid hydrocarbon fuel and a minor property-enhancing amount of a particular type of hydrocarbon-soluble dispersant or detergent. In another embodiment a method of reducing or inhibiting carburetor or injector deposits is provided. Particular novel and eminently useful dispersants or detergents suitable for use in hydrocarbon fuels constitute still another embodiment of this invention.

More particularly, this invention involves, inter alia, the discovery that by acylating an alkanol polyamine with a relatively short-chain acylating agent, a highly effective detergent for use in fuels can be formed without need for post-treatment such as is referred to and described for example in U.S. Pat. No. 4,780,111. Hence production and fuel treating costs can be kept to a minimum. Moreover, because the resultant acylated product has a relatively low molecular weight, its content of polar constituency can be relatively high on a weight basis. Thus a given quantity of a detergent of this invention can provide the same effectiveness in inhibiting deposit formation on critical engine parts such as carburetor nozzles and the like as a substantially larger quantity of a polyamine acylated with a long chain acylating agent of the type described heretofore. And the detergents of this invention have good fuel solubility, and exhibit little if any tendency to leave gums or residues in areas where the fuel is aspirated, as in the carburetor or in other similar parts of the fuel intake systems. Preferred embodiments of this invention involve the further discovery that certain structural configurations in the short chain acylating agents can provide acylated alkanol polyamine detergents of exceptional effectiveness in keeping certain fuel intake system parts essentially free of deposits.

In one of its more basic forms, this invention provides a fuel composition for an internal combustion engine, which composition comprises:
(i) a major amount of a liquid hydrocarbon fuel; and
(ii) a minor amount of a hydrocarbon-soluble detergent present in an amount sufficient to reduce the formation of carburetor or injector deposits, the detergent being prepared by reacting
  (a) at least one mono- or polycarboxylic acylating agent containing an average of from about 12 to about 50 carbon atoms in the molecule and having a acyclic aliphatic group containing an average of at least 12 (preferably at least 16) but less than 30 carbon atoms, with
  (b) at least one alkanol polyamine containing an average of at least 4 carbon atoms.

Pursuant to one preferred embodiment of this invention the acylating agent used in making the above detergent is at least one substituted succinic acid or acid derivative thereof (anhydride, acyl halide or lower alkyl ester) containing an average of from 16 to about 50 carbon atoms in the molecule and having a substantially straight chain acyclic aliphatic substituent group containing an average of at least 12 but less than 30, and preferably an average of at least 14 but no more than 28 carbon atoms.

In another preferred embodiment the acylating agent used in making the above detergent is at least one substituted succinic acid or acid derivative thereof containing an average of from 16 to about 50 carbon atoms in the molecule and having an acyclic aliphatic substituent group bifurcated on its beta carbon atom into two branches, one of which contains at least 4 carbon atoms and the other of which contains at least 6 carbon atoms, such substituent group containing an average of at least 12 but less than 30 carbon atoms.

Preferably, the alkanol polyamine used in forming the succimides with the preferred acylating agents referred to in the immediately preceding two paragraphs is one or mixture of alkanol polyamines represented by the general formula

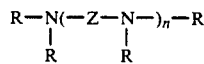

wherein Z is an alkylene group of from 2 to about 4 carbon atoms; each R is independently a hydrogen atom or an organic group which contains 1 to about 8 carbon atoms and is a hydrocarbyl, hydroxysubstituted hydrocarbyl, or primary amino-substituted hydrocarbyl group; and n is 1 to about 10; with the provisos that at least one R group is a hydroxy-substituted hydrocarbyl group, and that the compound contains at least one primary amino group. Use of 2-(2-aminoethylamino)ethanol is especially preferred.

In accordance with still another preferred embodiment, the detergent is a hydrocarbon-soluble substituted succinimide represented by the general formula

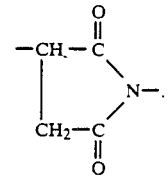

where R is alkylene of 2 to 4 carbon atoms, R' is a substantially straight chain alkyl or alkenyl group averaging at least 12 but less than 30 and preferably at least 14 but no more than 28 carbon atoms, R'' is a hydrogen atom or alkyl of 1 to 5 carbon atoms, and n is an integer in the range of 1 to 10.

In yet another preferred embodiment the detergent of this invention is a substituted succinimide represented by the general formula

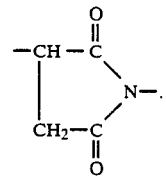

where R is alkylene of 2 to 4 carbon atoms, R' is an alkyl or alkenyl group bifurcated on its beta carbon atom into two branches one of which contains at least 4 carbon atoms and the other of which contains at least 6 carbon atoms, said group containing an average of at least 12 but less than 30 carbon atoms, R'' is a hydrogen atom or alkyl of 1 to 5 carbon atoms, and n is an integer in the range of 1 to 10.

These and other embodiments, features and advantages of this invention will become still further apparent from the ensuing description and appended claims.

The preferred fuels for use in the above fuel compositions of this invention are normally liquid hydrocarbon fuels in the gasoline boiling range, including hydrocarbon base fuels. The term "petroleum distillate fuel" also is used to describe the fuels which can be utilized in the fuel compositions of the present invention and which have the above characteristic boiling points. The term, however, is not intended to be restricted to straight-run distillate fractions. The distillate fuel can be straight-run distillate fuel, catalytically or thermally cracked (including hydrocracked) distillate fuel, or a mixture of straight-run distillate fuel, naphthas and the like with cracked distillate stocks. The hydrocarbon fuels also can contain non-hydrocarbonaceous materials such as alcohols, ethers, organo-nitro compounds, etc. Such materials can be mixed with the hydrocarbon fuel in varying amounts of up to about 10-20% or more. For example, alcohols such as methanol, ethanol, propanol and butanol, and mixtures of such alcohols are included in commercial fuels in amounts of up to about 10%. Other examples of materials which can be mixed with the fuels include diethyl ether, methyl ethyl ether, methyl tertiary butyl ether, and nitromethane. Also included within the scope of the invention are liquid fuels derived from vegetable or mineral sources such as corn, alfalfa, shale and coal. Also, the base fuels used in the formation of the fuel compositions of the present invention can be treated in accordance with well-known commercial methods, such as acid or caustic treatment, hydrogenation, solvent refining, clay treatment, etc.

Gasolines are supplied in a number of different grades depending on the type of service for which they are intended. The gasolines utilized in the present invention include those designed as motor and aviation gasolines. Motor gasolines include those defined by ASTM specification D-430-73 and are comprised of a mixture of olefins, paraffins, isoparaffins, naphthenes and occasionally diolefins. Motor gasolines normally have a boiling range within the limits of about 70° F. to 450° F. while aviation gasolines have narrower boiling ranges, usually within the limits of about 100° F.-330° F.

The fuel compositions of this invention contain a minor, property improving amount of at least one hydrocarbon-soluble detergent of the type described herein. The presence of such detergents in the fuel compositions of this invention provides the fuel composition with a desirable ability to prevent or minimize undesirable engine deposits, especially in the carburetor and fuel injector nozzles.

As noted above, the detergents used in such hydrocarbon fuels are made from one or more aliphatic or aromatic mono- or polycarboxylic acid acylating agents. As is well known, in reaction with co-reactive amines, such acylating agents may be used in the free acid form, in the form of a derivative thereof such as the anhydride, ester, acyl halide, or as a combination of any two or more of the foregoing.

The carboxylic acylating agent may be at least one aliphatic or aromatic mono- or polycarboxylic acid or such acid-producing compounds with the proviso that it contains an average of about 12-50 (preferably about 16-50 and most preferably about 20-50) carbon atoms in the molecule and has an acyclic aliphatic group of at least 12 but less than 30 carbon atoms.

Among the saturated and unsaturated aliphatic monocarboxylic acid acylating agents that may be used in producing the detergents of this invention are such compounds as dodecanoic acid, dodecenoic acid, tridecanoic acid, tridecenoic acid, tetradecanoic acid, palmitic acid, stearic acid, oleic acid, linoleic acid, linolenic acid, naphthenic acid, chlorostearic acid, tall oil acid, eicosanoic acid, elaidic acid, erucic acid, pentacosanoic acid, cerotic acid, etc., as well as the corresponding anhydrides, lower alkyl ($C_1$-$C_6$) esters, halides, or mixtures of any two or more of such materials.

The aliphatic monocarboxylic acids and anhydrides, etc. useful in this invention may be isoaliphatic acids, i.e., acids having one or more lower acyclic pendant groups. The isoaliphatic acids result in products which are more readily soluble in hydrocarbon fuels at relatively high concentrations and more readily miscible with other additives in the fuel. Such acids often contain a principal chain having from 14 to 20 saturated, aliphatic carbon atoms and at least one but no more than about four pendant acyclic alkyl groups. The principal chain of the acid is exemplified by groups derived from tetradecane, pentadecane, hexadecane, heptadecane, octadecane, and eicosane. The pendant group is preferably a lower alkyl radical such as methyl, ethyl, n-propyl, isopropyl, n-butyl, isobutyl, tert-butyl, n-hexyl, or other radical having less than about 6 carbon atoms.

The pendant group may also be a polar-substituted alkyl radical such as chloromethyl, bromobutyl, methoxyethyl, or the like, but it preferably contains no more than one polar substituent per radical. Specific examples of such acids are isoaliphatic acids such as 10-methyltetradecanoic acid, 11-methylpentadecanoic acid, 3-ethylhexadecanoic acid, 15-methylheptadecanoic acid, 16-methylheptadecanoic acid, 6-methyloctadecanoic acid, 8-methyloctadecanoic acid, 10-methyloctadecanoic acid, 14-methyloctadecanoic acid, 16-methyloctadecanoic acid, 15-ethylheptadecanoic acid, 3-chloromethylnonadecanoic acid, 7,8,9,10-tetramethyloctadecanoic acid, and 2,9,10-trimethyloctadecanoic acid.

A useful class of isoaliphatic acids includes mixtures of branched-chain acids prepared by the isomerization of commercial fatty acids. A useful method comprises the isomerization of an unsaturated fatty acid having from 16 to 20 carbon atoms, by heating it at a temperature above about 250° C. and at a pressure between about 200 and 700 psi (pounds per square inch), distilling the crude isomerized acid, and hydrogenating the distillate to produce a substantially saturated isomerized acid. The isomerization is promoted by a catalyst such as mineral clay, diatomaceous earth, aluminum chloride, zinc chloride, ferric chloride, or some other Friedel-Crafts catalyst. The concentration of the catalyst may be as low as 0.01%, but more often is from 0.1% to 3% by weight of the isomerization mixture. Water also promotes the isomerization and a small amount—e.g., from 0.1% to 5% by weight—of water may thus be advantageously added to the isomerization mixture.

The unsaturated fatty acids from which the isoaliphatic acids may be derived include oleic acid, linoleic acid, linolenic acid, or commercially fatty acid mixtures such as tall oil acids containing a substantial proportion of unsaturated fatty acids.

The aliphatic polycarboxylic acids useful as acylating agents include dicarboxylic acids and derivatives which have an aliphatic substituent of at least 12 but less than 30 carbon atoms, such that the acylating agent contains up to about 50 carbon atoms (preferably about 16 to about 50 carbon atoms). Examples of such compounds include tridecylsuccinic acid, pentadecylsuccinic acid, tetradecenylsuccinic acid, hexadecenylsuccinic acid, dodecylsuccinic acid, tetradecylsuccinic acid, hexadecylsuccinic acid, octadecenylsuccinic acid, tetrapropylene-substituted succinic acid, docosenylsuccinic acid, similarly substituted chlorosuccinic acids, similarly substituted malonic acids, similarly substituted glutaric acids, similarly substituted adipic acids, and similarly substituted pimelic, azeleic, sebacic, glutaconic, citraconic, and itaconic acids, etc., as well as anhydrides, acyl halides, and lower alkyl esters of such acids, and including any mixture of two or more of any such materials. Preferred polycarboxylic acid acylating agents are alkyl and/or alkenyl succinic anhydrides in which the alkyl or alkenyl group is substantially straight chain in configuration and contains 12 to 26 carbon atoms, and more preferably an average of about 18 to about 24 carbon atoms. An especially preferred acylating agent of this type is octadecenylsuccinic acid or anhydride.

Still another preferred acylating agent is an alkyl- or alkenylsuccinic acid or anhydride in which the alkyl or alkenyl group is bifurcated on the beta-carbon atom and is composed of two substantially linear chains. Preferred alkyl groups of this type may be represented by the formula

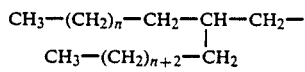

where n is an integer in the range of 2 to 10. A preferred group of such bifurcated alkenyl groups may be represented by the formula

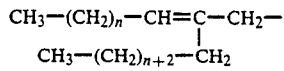

where n is an integer in the range of 2 to 10. It will be understood and appreciated that the double bond in such alkenyl group may be isomerized to different positions from that depicted (which is the preferred position) by treating the alkenylsuccinic acid or anhydride with an isomerization catalyst such as silica gel, a trialkylborane, or the like. Such alkyl- and alkenylsubstituted succinic acids and anhydrides can be formed from dimerized 1-olefins such as by dimerizing 1-hexene, 1-heptene, 1-octene, 1-nonene, 1-decene, 1-undecene, 1-dodecene, 1-tetradecene, 4-methyl-1-pentene, 6-methyl-1-heptene, 5-ethyl-1-decene, or 3,5,5-trimethyl-1-undecene with an aluminum alkyl dimerization catalyst according to known procedures. See for example Ziegler et al, *Ann.* 629, 121–166 (1960) all disclosure of which is incorporated herein by reference. The resultant dimerized olefin (sometimes referred to as a vinylidene olefin) is then used to alkylate maleic anhydride or an ester of maleic acid, etc., to form the alkenyl-substituted succinic acid compound by the "ene" reaction. See in this connection Hoffman, *Angew. Chem., Int. Ed.* (English), 8, 556–577 (1969); Snider, *J. Org. Chem.,* 39, 255 (1974); and Keung et al, *J. Chem. Educ.,* 49. 97–100 (1972), all disclosures of which are incorporated herein by reference. As is well known, the "ene" reaction may be facilitated by the use of a catalyst such as aluminum trichloride, alkyl aluminum sesquichloride or the like. To form the bifurcated alkyl substituent, the bifurcated alkenyl group of the resultant alkenyl-substituted succinic acid compound may be hydrogenated to saturate the double bond.

Similarly suitable alkyl- or alkenylsuccinic acids or anhydrides in which the alkyl or alkenyl group is bifurcated on the beta-carbon atom into two branches can be formed in analogous fashion using co-dimerized 1-olefin such as by co-dimerizing 1-butene and 1-octene, 1-hexene and 1-decene, 1-pentene and 1-dodecene, 4-methyl-1-pentene and 1-tetradecene, 1-octene and 1-decene, 1-nonene and 1-decene, 1-decene and 1-dodecene, 1-dodecene and 1-tetradecene, 2,7-dimethyl-1-octene and 1-decene, 2,7-dimethyl-1-octene and 1-dodecene, 1-tetradecene and 1-pentadecene, etc., using a co-dimerization catalyst such as an aluminum alkyl. Such co-dimerized olefins are then used in the "ene" reaction in the same manner as described above. Hydrogenation of the alkenyl succinic acid compound (anhydride, ester, etc.) yields the corresponding bifurcated alkyl succinic acid compound.

The acylating agent may contain polar substituents provided that the polar substituents are not present in proportions sufficiently large to alter significantly the hydrocarbon character of the acylating agent. Typical suitable polar substituents include halo, such as chloro and bromo, oxo, oxy, formyl, sulfenyl, sulfinyl, thio, nitro, etc. Such polar substituents, if present, preferably do not exceed 10% by weight of the total weight of the hydrocarbon portion of the acylating agent, exclusive of the carboxyl groups.

Reference may be had, for example to U.S. Pat. Nos. 3,087,936; 3,163,603; 3,172,892; 3,219,666; 3,272,746; 3,306,907; 3,346,354; and 4,234,435 for synthesis procedures which may be used, or modified for use, in preparing the hydrocarbonsubstituted acylating agents with the proviso of course that the materials used result in the production of an acylating agent containing an average of up to about 50 carbon atoms and having an acyclic aliphatic group of at least about 12 but less than 30 carbon atoms. In the interest of brevity, these patents are incorporated herein for their disclosure of suitable synthesis procedures which may be adapted for use in producing such mono- and polycarboxylic acid acylating agents.

As disclosed in the foregoing patents, there are several processes for preparing the acids. As utilized in this invention, the process involves the reaction of (1) an ethylenically unsaturated carboxylic acid, acid halide, or anhydride with (2) an ethylenically unsaturated hydrocarbon containing at least about 12 but less than 30 aliphatic carbon atoms or a chlorinated hydrocarbon containing at least about 12 but less than 30 aliphatic carbon atoms at a temperature within the range of about 100°–300° C. The chlorinated hydrocarbon or ethylenically unsaturated hydrocarbon reactant can, of course, contain polar substituents, short chain alkyl (e.g., methyl, ethyl, etc.) pendant groups, and/or additional non-conjugated unsaturation. It is these hydrocarbon reactants which provides most of the aliphatic carbon atoms present in the acyl moiety of the final products.

When preparing the carboxylic acid acylating agent according to one of these two processes, the carboxylic acid reactant usually corresponds to the formula $R'(COOH)_n$, where $R'$ is characterized by the presence of at least one ethylenically unsaturated carbon-to-carbon covalent bond and n is an integer from 1 to 6 and preferably 1 or 2. The acidic reactant can also be the corresponding carboxylic acid halide, anhydride, ester, or other equivalent acylating agent and mixtures of one or more of these. Ordinarily, the total number of carbon atoms in the acidic reactant will not exceed 10 and generally will not exceed 6. Preferably the acidic reactant will have at least one ethylenic linkage in an alpha, beta-position with respect to at least one carboxyl function. Exemplary acidic reactants are acrylic acid, methacrylic acid, maleic acid, maleic anhydride, fumaric acid, itaconic acid, itaconic anhydride, citraconic acid, citraconic anhydride, mesoconic acid, glutaconic acid, chloromaleic acid, aconitic acid, crotonic acid, methylcrotonic acid, sorbic acid, 2-hexenoic acid, 2-decenoic acid, and the like. Due to considerations of economy and availability, these acid reactants usually employed are acrylic acid, methacrylic acid, maleic acid, and maleic anhydride.

As is apparent from the foregoing discussion, the carboxylic acid acylating agents may contain cyclic and/or aromatic groups. However, the acids are essentially aliphatic in nature and in most instances, the preferred acid acylating agents are aliphatic mono- and polycarboxylic acids, anhydrides, and acyl halides.

The substantially saturated aliphatic hydrocarbon-substituted succinic acid and anhydrides are especially preferred as acylating agents used as starting materials in the present invention. The succinic acid acylating agents are readily prepared by reacting maleic anhydride with an olefin or a chlorinated hydrocarbon of suitable chain length such as a chlorinated polyolefin. The reaction involves merely heating the two reactants at a temperature of about 100°–300° C., preferably, 100°–200° C. The product from such a reaction is a substituted succinic anhydride where the substituent is derived from the olefin or chlorinated hydrocarbon as described in the above-cited patents. The product may be hydrogenated to remove all or a portion of any ethylenically unsaturated covalent linkages by standard hydrogenation procedure, if desired. The substituted succinic anhydrides may be hydrolyzed by treatment with water or steam to the corresponding acid and either the anhydride or the acid may be converted to the corresponding acid halide or ester by reacting with phosphorus halide, phenols, or alcohols.

The ethylenically unsaturated hydrocarbon reactant and the chlorinated hydrocarbon reactant used in the preparation of the acylating agents are principally olefins, olefin oligomers, substantially saturated petroleum fractions and substantially saturated olefin oligomers and the corresponding chlorinated products. They contain an average of from 12 to below about 30 carbon atoms in the molecule. The oligomers and chlorinated oligomers derived from mono-olefins having from 2 to about 4 carbon atoms are preferred. The especially useful oligomers are the oligomers of such 1-monoolefins as ethylene, propene, 1-butene, and isobutene. Oligomers of medial olefins, i.e., olefins in which the olefinic linkage is not at the terminal position, likewise are useful. These are exemplified by 2-butene.

The low molecular weight interoligomers of 1-monoolefins such as illustrated above with each other and with other inter-oligomerizable olefinic substances are also useful sources of the ethylenically unsaturated reactant. Such interoligomers contain an average from 12 to below about 30 carbon atoms in the molecule, and include for example, those prepared by oligomerizing ethylene with propene, ethylene with isobutene, and ethylene with 1-butene, etc.

The chlorinated hydrocarbons and chlorinated ethylenically unsaturated hydrocarbons used in the preparation of the acylating agents also contain an average of 12 to below about 30 carbon atoms in the molecule. The preferred reactants are the above-described olefins and chlorinated olefins containing an average of at least 16 carbon atoms, preferably about 16 to about 28 carbon atoms.

The acylating agents may also be prepared by halogenating a hydrocarbon such as the above-described olefin oligomers to produce a polyhalogenated product, converting the polyhalogenated product to a polynitrile, and then hydrolyzing the polynitrile. They may be prepared by oxidation of a polyhydric alcohol with potassium permanganate, nitric acid, or a polycarboxylic acids involves the reaction of an olefin or a polar-substituted hydrocarbon such as a monochloroisobutene oligomer with an unsaturated polycarboxylic acid such as 2-pentene-1,3,5-tricarboxylic acid prepared by dehydration of citric acid.

Monocarboxylic acid acylating agents may be obtained by oxidizing a monoalcohol with potassium permanganate or by reacting a halogenated olefin oligomer with a ketene. Another convenient method for preparing monocarboxylic acid involves the reaction of metallic sodium with an acetoacetic ester or a malonic ester of an alkanol to form a sodium derivative of the ester and the subsequent reaction of the sodium derivative of the ester with a halogenated hydrocarbon such as brominated paraffin or brominated polyisobutene of suitable chain length.

Monocarboxylic and polycarboxylic acid acylating agents can also be obtained by reacting chlorinated mono- and polycarboxylic acids, anhydrides, acyl halides, and the like with ethylenically unsaturated hydrocarbons or ethylenically unsaturated substituted hydrocarbons such as the polyolefins and substituted polyolefins of suitable molecular weight (average of $C_{12}$ to below about $C_{30}$) but otherwise using procedures of the type described in U.S. Pat. No. 3,340,281.

The monocarboxylic and polycarboxylic acid anhydrides are obtained by dehydrating the corresponding acids. Dehydration is readily accomplished by heating the acid to a temperature above about 70° C., preferably in the presence of a dehydration agent, e.g., acetic anhydride. Cyclic anhydrides are usually obtained from polycarboxylic acids having acid radicals separated by no moire than three carbon atoms such as substituted succinic or glutaric acid, whereas linear anhydrides are obtained from polycarboxylic acids having the acid radicals separated by four or more carbon atoms.

The acid halides of the monocarboxylic and polycarboxylic acids can be prepared by the reaction of the acids or their anhydrides with a halogenating agent such as phosphorus tribromide, phosphorus pentachloride, or thionyl chloride.

Although it is preferred that the acylating agent is an aliphatic mono- or polycarboxylic acid, and more preferably a dicarboxylic acid, the carboxylic acylating agent also may be an aromatic mono- or polycarboxylic acid or acid-producing compound. The aromatic acids are principally mono- and dicarboxysubstituted benzene, naphthalene, anthracene, phenanthrene or like aromatic hydrocarbons in which an aromatic ring is alkylsubstituted. The alkyl groups may contain up to about 29 carbon atoms so long as the acylating agent contains an average of no more than about 50 carbon atoms. The aromatic acid may also contain other substituents such as halo, hydroxy, lower alkoxy, etc. Specific examples of aromatic mono- and polycarboxylic acids and acid-producing compounds useful as acylating agent include the alkyl-substituted derivatives of such acids as benzoic acid, m-toluic acid, salicyclic acid, phthalic acid, isophthalic acid, terephthalic acid, 4-propoxybenzoic acid, 4-methylbenzene-1,3-dicarboxylic acid, naphthalene-1,4-dicarboxylic acid, anthracene dicarboxylic acid, 3-dodecylbenzene-1,4-dicarboxylic acid, 2,5-dibutylbenzene-1,4-dicarboxylic acid, etc. The anhydrides of these dicarboxylic acids also are useful as the carboxylic acylating agent.

The other reactant used in the formation of the detergents of this invention is one or a mixture of alkanol polyamines containing in the molecule an average of at least 4 carbon atoms, for example an average in the range of 4 to about 50, and preferably from 4 to about 20 carbon atoms. Such compounds may be represented by the general formula

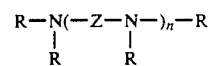

wherein Z is an alkylene group of from 1 to about 8 carbon atoms (preferably from 2 to 4 carbon atoms); each R is independently a hydrogen atom, or (a) a hydrocarbyl group, or (b) a hydroxysubstituted hydrocarbyl group, or (c) a primary amino-substituted hydrocarbyl group, in which the groups of (a), (b), or (c) contain from 1 to about 8 carbon atoms (preferably from 2 to 4 carbon atoms); and n is 1 to about 10; with the proviso that at least one R group is a hydrogen atom such that the compound is co-reactive with the carboxylic acylating agent being employed therewith, and the proviso that at least one R group is a hydroxy-substituted hydrocarbyl group. Preferably the compound contains at least one primary amino group.

Preferably, n is an integer less than about 6, and the alkylene group (Z) is preferably a lower alkylene group such as dimethylene, trimethylene, tetramethylene, etc.

Examples of such alkanol polyamines include alkanol polyamines having at least one primary amino group in the molecule such as, for example, N-(2-hydroxyethyl)ethylene diamine (also known as 2-(2-aminoethylamino)ethanol), 2-(2-aminoethylamino)-1-methylethanol, 2-(2-aminoethylamino)-2-methylethanol, 2-(2-aminoethylamino)-1-ethylethanol, 2-(2-aminoethylamino)-2-ethylethanol, 2-(2-aminoethylamino)-1,2-dimethylethanol, N-(2-hydroxyethyl)diethylene triamine, N-(2-hydroxyethyl)triethylene tetramine, N-(2-hydroxyethyl)tetraethylene pentamine, N-(2-hydroxyethyl)pentaethylene hexamine, N-(2-hydroxy-1methylethyl)diethylene triamine, N-(2-hydroxy-2-methylethyl)diethylene triamine, N-(2-hydroxy-1-methylethyl)triethylene tetramine, N-(2-hydroxy-2-methylethyl)triethylene tetramine, N-(2-hydroxy-1-methylethyl)tetraethylene pentamine, N-(2-hydroxy-2-methylethyl)tetraethylene pentamine, N-(2-hydroxy-1-methylethyl)pentaethylene hexamine, N-(2-hydroxy-2-methylethyl)pentaethylene hexamine, N-(2-hydroxy-1-butyl)triethylene tetramine, N-(1-hydroxy-2-butyl)triethylene tetramine, N-(3-hydroxy-2-butyl)triethylene tetramine, N-(2-hydroxy-1-butyl)tetraethylene pentamine, N-(1-hydroxy-2-butyl)tetraethylene pentamine, N-(3-hydroxy-2-butyl)tetraethylene pentamine, N-(2-hydroxyethyl)trimethylene diamine, N-(2-hydroxyethyl)tetramethylene diamine, N-(2-hydroxyethyl)pentamethylene diamine, N-(2-hydroxyethyl)hexamethylene diamine, N-(2-hydroxyethyl)tetraminoneopentane, N,N'-bis(2-hydroxyethyl)tetraaminoneopentane, N,N',N''-tris(2-hydroxyethyl)tetraaminoneopentane, N,N-di(2-hydroxyethyl)ethylene diamine, N-(hydroxymethyl)ethylene diamine, N-(8-hydroxyoctyl)ethylene diamine, N-(8-hydroxy-2,7-dimethyloctyl)ethylene diamine, and the like. Use may also be made of alkanol secondary polyamines (i.e., compounds which, while devoid of a primary amino group, do contain at least one secondary amino group), a few illustrative examples of which include such compounds as N,N'-bis(2-hydroxyethyl)ethylene diamine, N-(2-hydroxyethyl)piperazine, N,N'-bis(2-hydroxyethyl)trimethylene diamine, N,N'-bis(2-hydroxyethyl)tetramethylene diamine, N,N'-bis(2-hydroxyethyl)pentamethylene diamine, N,N'-bis(2-hydroxyethyl)hexamethylene diamine, N,N''-bis(2-hydroxy-1-methylethyl)diethylene triamine, N,N''''-(2-hydroxy-2-methylethyl)triethylene tetramine, N,N''''-(3-hydroxy-2-butyl)triethylene tetramine, N,N',N''-tris(2-hydroxy-1-methylethyl)diethylene triamine, N,N'-(hydroxymethyl)ethylene diamine, N,N'-bis(6-hydroxyhexyl)ethylene diamine, N,N''-bis(8-hydroxy-2,7-dimethyloctyl)diethylene triamine, and the like.

The principal bonding as between the reactants is believed to depend at least in part upon the type of carboxylic acylating agent(s) and type of alkanol polyamine(s) employed in the reaction. Thus when employing one or more polycarboxylic acylating agents with one or more alkanol polyamines having at least one primary amino group in the molecule co-reactive therewith, imide-type bonding predominates. In the case of reactions between one or more monocarboxylic acylating agents with one or more alkanol polyamines having at least one primary amino group in the molecule, it is believed that unless forcing reaction conditions are used, the predominant type of bonding involves amide-type bonding, perhaps with some imide formation also occurring. In reactions between one or more monocarboxylic and/or polycarboxylic acylating agents with one or more alkanol polyamines having no primary amino group in the molecule but containing at least one secondary amino group co-reactive with the acylating agent(s) being employed, the predominant bonding is believed to involve amide-type bonding. Irrespective of their precise composition, the acylated alkanol polyamine detergents of this invention are useful for the purposes of this invention.

The ratio of reactants utilized in the preparation of the dispersants may be varied over a wide range. Generally, the reaction mixture will contain, for each equivalent of the acylating agent, at least about 0.5 equivalent of the alkanol polyamine. The upper limit of the alkanol polyamine reactant is about 2 equivalents per equivalent of the acylating agent. The preferred amounts of the reactants are from about 1 to about 2 equivalents of the alkanol polyamine for each equivalent of the acylating agent.

The equivalent weight of the alkanol polyamine is based on the number of amino groups per molecule, and the equivalent weight of the acylating agents is based on the number of carboxy groups per molecule. To illustrate N-(2-hydroxyethyl)ethylene diamine has from 1 to 2 equivalents per mole, and N-(2-hydroxyethyl) tetraethylene pentamine has from 1 to 5 equivalents per mole. The monocarboxylic acids have one carboxy group, and therefore the equivalent weight of the monocarboxylic acids is its molecular weight. The succinic and aromatic dicarboxylic acid acylating agents, on the other hand, have two carboxy groups per molecule, and therefore, the equivalent weight of each is one-half its molecular weight. In most cases, the equivalent weight of the polyamine is determined by its nitrogen content, and the equivalent weight of acylating agents is determined by their acidity or potential acidity as measured by the neutralization or saponification equivalents.

The temperature of the reaction used to prepare the dispersants useful in the fuels of this invention is not critical, and generally, any temperature from room temperature up to the decomposition temperature of any of the reactants or the product can be utilized. Preferably, however, the temperature will be above about 50° C. and more generally from about 100° C. to about 250° C.

When preparing the dispersant-detergents of this invention, a mixture of one or more of the acylating agents and one or more of the alkanol polyamines is heated optionally in the presence of a normally liquid, substantially inert organic liquid solvent/diluent. The reaction temperature will be, as defined above, generally above 50° C. up to the decomposition temperature of any of the reactants or of the product. The reaction of the acylating agent with the alkanol polyamine is accompanied by the formation of approximately one mole of water for each equivalent of the acid used. The removal of water formed may be effected conveniently by heating the product at a temperature above 100° C., preferably in the neighborhood of about 150° C. Removal of the water may be facilitated by blowing the reaction mixture with an inert gas such as nitrogen during heating. It may likewise be facilitated by the use of a solvent which forms an azeotrope with water. Such solvents are exemplified by benzene, toluene, naphtha, n-hexane, xylene, etc. The use of such solvents permits the removal of water at a lower temperature, e.g., 80° C.

In another embodiment of this invention, middle distillate (diesel) fuel compositions are provided containing detergents of the type describe above. Preferably the acyclic aliphatic substituent of the acylating agent for the detergents of these compression ignition engine fuel compositions is an alkyl or alkenyl group containing from 16 to 18 carbon atoms. Octadecenylsuccinic acid or anhydride is a particularly preferred acylating agent for making such detergents. Of the various hydroxyalkyl polyamines referred to hereinabove, 2-(2-aminoethylamino)ethanol is particularly preferred for making the detergents for diesel fuel usage.

Yet another aspect of this invention is a method for reducing deposits, especially carburetor and/or injector deposits, in an internal combustion engine, which method comprises: (i) blending with a major amount of a liquid hydrocarbon fuel a minor amount of a hydrocarbon-soluble detergent sufficient to reduce the formation of engine deposits, the detergent being prepared by reacting (a) at least one mono- or polycarboxylic acylating agent containing an average of from about 12 to about 50 carbon atoms in the molecule and having an acyclic aliphatic group containing an average of at least 12 but less than 30 carbon atoms, with (b) at least one alkanol polyamine containing an average of at least 4 carbon atoms; and (ii) using the fuel composition in an internal combustion engine.

The following Examples illustrate the preparation of the dispersant-detergents of this invention. Unless otherwise indicated in the following examples and elsewhere in the specification and claims, all parts and percentages are by weight.

EXAMPLE 1

To a reactor equipped with a stirrer, a Dean-Stark trap and a condenser are added 159 parts of octadecenylsuccinic anhydride and 87 parts of xylene (mixed isomers). To this mixture are added 47 parts of 2-(2-aminoethylamino)ethanol and 52 parts of xylene. The resultant mixture is heated to reflux with stirring until all of the water formed in the reaction has been collected in the Dean-Stark trap (ordinarily in about 2.5 hours). The reaction mixture is indicated by infra-red to contain succinimide. The product is then stripped to 150° C. at 5 mm Hg vacuum. The residue is about 190 parts of predominantly $C_{18}$ alkenylsuccinimide of 2-(2-aminoethylamino)ethanol. Such product may be represented by the formula

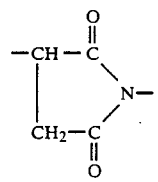

where R' is $C_{18}$ alkenyl.

EXAMPLE 2

Using the procedure and apparatus as described in Example 1 above, 116 parts of mixed $C_{16}$- and $C_{18}$-alkenylsuccinic anhydrides (average molecular weight of approximately 328) are reacted with 37.3 parts of 2-(2-aminoethylamino)ethanol in 130 parts of xylene. After the stripping operation, approximately 140 parts of product residue is recovered. This acylated product is predominantly a mixture of succinimides as depicted in Example 1 wherein R' is composed of $C_{16}$ and $C_{18}$ alkenyl groups.

EXAMPLE 3

To a reactor equipped as in Example 1 above are charged 56 parts of branched $C_{16}$-alkenylsuccinic anhydride (in which the alkenyl group is formed from dimerized 1-octene) and 52 parts of xylene. Then 16.8 parts of 2-(2-aminoethylamino)ethanol and 35 parts of xylene are charged into the reactor, and the resultant mixture is heated with stirring to reflux while azeotropically removing the water formed during the reaction. After collecting 3 parts of water (theory is about 2.8 parts) the product mixture is stripped at 35 mm Hg vacuum to 170° C. The residual acylated product (approximately 59 parts) is predominantly an alkenylsuccinimide of the formula

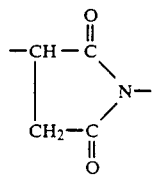

EXAMPLE 4

To a reactor equipped as in Example 1 above are charged 50 parts of branched $C_{20}$-alkenylsuccinic anhydride (in which the alkenyl group is formed from dimerized 1-decene) and 35 parts of xylene. Then 14.3 parts of 2-(2-aminoethylamino)ethanol and 52 parts of xylene are charged into the reactor, and the resultant mixture is heated with stirring to reflux while azeotropically removing the water formed during the reaction. After collecting about 2.5 parts of water (theory is about 2.4 parts) the product mixture is stripped at 35 mm Hg vacuum to 170° C. The residual acylated product (approximately 59.9 parts) is predominantly an alkenylsuccinimide of the formula

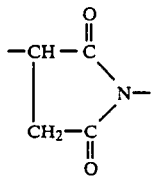

EXAMPLE 5

The procedure of Example 3 above is repeated using 50 parts of a mixture of $C_{16}$-, $C_{18}$-, $C_{20}$-, $C_{22}$-, $C_{24}$-, and $C_{26}$-alkenylsuccinic anhydrides and 15.5 parts of 2-(2-aminoethylamino)ethanol in 87 parts of refluxing xylene. The olefin mixture from which this alkenyl succinic anhydride reactant is made is composed, on a weight basis, of 0.8% $C_{16}H_{32}$, 8.2% $C_{18}H_{36}$, 42.2% $C_{20}H_{40}$, 33.3% $C_{22}H_{44}$, 14.7% $C_{24}H_{48}$ and 0.8% $C_{26}H_{52}$. After stripping the reaction mixture, a product composed predominantly of a mixture of $C_{16-26}$-alkenylsuccinimides of 2-(2-aminoethylamine)ethanol is recovered. The alkenyl groups of this succinimide product are in proportions averaging in the range of from between about $C_{20}$ to about $C_{22}$.

EXAMPLE 6

Using the general procedure of Example 1 above, a mixture of $C_{22}$- and $C_{24}$-alkenylsuccinic anhydrides with an average molecular weight of 440 and 2-(2-aminoethylamino)ethanol in equimolar quantities are reacted in refluxing xylene with removal of by-product water. The product remaining after the stripping operation is predominantly an acylated compound as depicted in Example 1 above wherein R' is docosenyl ($C_{22}$) and tetracosenyl ($C_{24}$).

EXAMPLE 7

By use of the procedure of Example 1 above, 50 parts of a $C_{18}$ alkenyl-substituted succinic anhydride is reacted with 33 parts of N-(2-hydroxy-1-methylethyl)tetraethylene pentamine in 100 parts of refluxing xylene. The product remaining after the stripping operation is predominantly a $C_{18}$ alkenylsuccinimide of N-(2-hydroxy-1-methylethyl)tetraethylene pentamine.

EXAMPLE 8

The procedure of Example 1 above is repeated using 50 parts of a $C_{12}$ alkenyl-substituted succinic anhydride and 48 parts of an equimolar mixture of N-(2-hydroxyethyl)diethylene triamine and N-(2-hydroxyethyl)triethylene tetramine in 100 parts of refluxing xylene. After stripping, a product composed predominantly of a mixture of $C_{12}$ alkenylsuccinimides of N-(2-hydroxyethyl)diethylene triamine and N-(2-hydroxyethyl)triethylene tetramine is recovered.

EXAMPLE 9

Repetition of the procedure of Example 1 above is done using 159 parts of a $C_{18}$ alkenyl-substituted succinic anhydride and 73 parts of N-(2-hydroxyethyl)hexamethylene diamine in 150 parts of refluxing xylene. After stripping, a product composed predominantly of $C_{18}$ alkenylsuccinimide of N-(2-hydroxyethyl)hexamethylene diamine is recovered.

EXAMPLE 10

While continuously blowing the reaction mixture with nitrogen to remove volatiles, 34.1 parts of isostearic acid is slowly added over a two-hour period to 16.2 parts of N-(2-hydroxyethyl)diethylene triamine heated at 100° C. The mixture is then heated to and held at 150° C. for one hour, heated to 180° C. over an additional hour, and then heated to 205° C. over a period of 0.5 hour. The mixture is held at 205°–230° C. for a total of 11.5 hours and then stripped at 230° C. and 20 mm Hg pressure thereby providing the desired acylated alkanol polyamine.

The effectiveness of the fuel compositions of this invention in reducing carburetor deposits was demonstrated by a series of standard CRC carburetor tests. On completion of each such engine test the weight of deposits formed on the carburetor sleeve during the test was measured. Thus the lower the weight, the more effective was the fuel composition. The same base fuel was used in each series of tests, and the additives employed therein and results obtained are summarized in Tables I–III below. All additive concentrations are expressed therein as pounds per thousand barrels (ptb). Baseline runs were conducted before and after the runs on the fuels of this invention and the values shown in the tables are the averages of such before and after runs.

TABLE I

| Additive | Additive Conc., ptb | Sleeve Wt., mg | % Reduction |
|---|---|---|---|
| None | — | 27.2 | — |
| Ex. 1 | 10 | 1.8 | 93.4 |
| Ex. 2 | 10 | 9.4 | 65.4 |

TABLE II

| Additive | Additive Conc., ptb | Sleeve Wt., mg | % Reduction |
|---|---|---|---|
| None | — | 23.9 | — |
| Ex. 1 | 5 | 9.4 | 60.7 |
| Ex. 2 | 5 | 12.7 | 46.9 |

TABLE III

| Additive | Additive Conc., ptb | Sleeve Wt., mg | % Reduction |
|---|---|---|---|
| None | — | 22.5 | — |
| Ex. 1 | 10 | 2.0 | 91.1 |
| Ex. 3 | 10 | 3.7 | 83.6 |
| Ex. 4 | 10 | 2.7 | 88.0 |
| Ex. 5 | 10 | 3.4 | 84.9 |
| Ex. 6 | 10 | 5.1 | 77.3 |

The amount of the detergent included in the fuel compositions of this invention may vary over a wide range although it is preferred not to include unnecessarily large excesses of the detergent. The amount included in the fuel should be an amount sufficient to improve the desired properties such as the prevention and/or reduction in the amount of deposits on the various parts of internal combustion engines such as in the carburetor and the fuel injector nozzles when the fuel is used to operate internal combustion engines. The fuel may contain from about 1 to about 10,000, and preferably from about 5 to about 5000 parts per million parts by weight of the fuel. The detergents utilized in the fuel compositions of this invention are hydrocarbon-soluble in the sense that the detergents are at to provide a solution containing the desired concentrations specified above.

The fuel compositions of this invention can be prepared by adding the detergents to a liquid hydrocarbon fuel, or a concentrate of the detergent in a substantially inert, normally liquid organic solvent/diluent such as mineral oil, xylene, or a normally liquid fuel as described above can be prepared, and the concentrate added to the liquid hydrocarbon fuel. The concentrates generally contain about 5-95, usually 10-90% of the detergent of the invention, and the concentrate can also contain any of the conventional additives for fuels such as those described below.

In addition to the detergent of this invention, the use of other conventional fuel additives in the fuel compositions (and concentrates) of the present invention is contemplated and is within the ambit of this invention. Thus, the fuels can contain antiknock agents such as tetraalkyllead compounds, organomanganese additives such as methylcyclopentadienylmanganes tricarbonyl, lead scavengers such as haloalkanes (e.g., ethylene dichloride and ethylene dibromide), deposit preventors or modifiers such as trialkyl or triaryl phosphates, dyes, antioxidants such as 2,6-di-tert-butyl-4-methyl phenol, rust-inhibitors such as alkylated succinic acids and anhydrides, gum inhibitors, metal deactivators, demulsifiers, upper cylinder lubricants, anti-icing agents, etc. The middle distillate or diesel fuels may contain ignition accelerators such as alkyl nitrates, combustion improvers such as methylcyclopentadienylmanganese tricarbonyl, alcohols, corrosion inhibitors, antioxidants, stabilizers, particulate reducing additives, and the like.

This invention is susceptible to considerable variation in its practice within the spirit and scope of the ensuing claims, the embodiments described hereinbefore being illustrative, but not limitative, of its practice.

What is claimed is:

1. A fuel composition for an internal combustion engine, which composition comprises:
   (i) a major amount of a liquid hydrocarbon fuel of the gasoline boiling range; and
   (ii) a minor amount of a hydrocarbon-soluble detergent present in an amount sufficient to reduce the formation of carburetor and/or injector deposits, the detergent being prepared by the process consisting essentially of reacting
      (a) at least one aliphatic hydrocarbon-substituted succinic acid or anhydride acylating agent containing an average of from about 12 to about 50 carbon atoms in the molecule and having an acyclic aliphatic hydrocarbon substituent group containing an average of at least 12 but less than 30 carbon atoms, with
      (b) at least one alkanol polyamine containing an average of at least 4 carbon atoms.

2. A fuel composition of claim 1 wherein the alkanol polyamine contains an average of from 4 to 20 carbon atoms.

3. A fuel composition of claim 1 wherein the hydrocarbon-soluble detergent is present in the fuel composition in an amount in the range of from about 5 to about 5,000 parts by weight per million parts by weight of the fuel.

4. A fuel composition of claim 1 wherein the alkanol polyamine contains an average of from 4 to 10 carbon atoms.

5. A fuel composition of claim wherein the acylating agent is predominantly or entirely an alkyl- or alkenyl-substituted succinic acid or anhydride in which the alkyl- or alkenyl substituent contains an average of at least 16 carbon atoms.

6. A fuel composition of claim 1 wherein the acylating agent is predominantly or entirely octadecenylsuccinic acid or anhydride.

7. A fuel composition of claim 1 wherein the acylating agent is predominantly or entirely hexadecenylsuccinic acid or anhydride.

8. A fuel composition of claim 1 wherein the acylating agent is predominantly or entirely a mixture of $C_{16}$, $C_{18}$, $C_{20}$, $C_{22}$, $C_{24}$ and $C_{26}$ alkenyl-substituted succinic acids or anhydrides.

9. A fuel composition of claim 1 wherein the acylating agent is at least one succinic acid or anhydride and wherein the acyclic aliphatic group of such acylating agent is a substantially straight chain acyclic aliphatic group.

10. A fuel composition of claim 1 wherein the acylating agent is predominantly or entirely an alkenylsuccinic acid or anhydride in which the alkenyl group has the formula

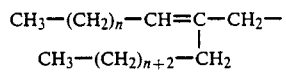

where n is an integer in the range of 2 to 10.

11. A fuel composition of claim 1 wherein the acylating agent is predominantly or entirely an alkenylsuccinic acid or anhydride in which the alkenyl group has the formula

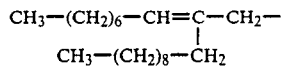

12. A fuel composition of claim 1 wherein the acylating agent is predominantly or entirely an alkenylsuccinic acid or anhydride in which the alkenyl group has the formula

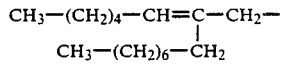

13. A fuel composition of claim 1 wherein the acylating agent is predominantly or entirely octadecenylsuccinic acid or anhydride and wherein the alkanol polyamine consists essentially of 2-(2-aminoethylamino)ethanol.

14. A fuel composition of claim 1 wherein the acylating agent is predominantly or entirely hexadecenylsuccinic acid or anhydride and wherein the alkanol polyamine consists essentially of 2-(2-aminoethylamino)ethanol.

15. A fuel composition of claim 1 wherein the acylating agent is predominantly or entirely a mixture of $C_{16}$, $C_{18}$, $C_{20}$, $C_{22}$, $C_{24}$, and $C_{26}$ alkenyl-substituted succinic acids or anhydrides and wherein the alkanol polyamine consists essentially of 2-(2-aminoethylamino)ethanol.

16. A fuel composition of claim 1 wherein the acylating agent is at least one succinic acid or anhydride and wherein the acyclic aliphatic group of such acylating agent is a substantially straight chain acyclic aliphatic group and wherein the alkanol polyamine consists essentially of 2-(2-aminoethylamino)ethanol.

17. A fuel composition of claim 1 wherein the acylating agent is predominantly or entirely an alkenylsuccinic acid or anhydride in which the alkenyl group has the formula

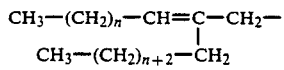

wherein n is an integer in the range of 2 to 10, and wherein the alkanol polyamine consists essentially of 2-(2-aminoethylamino)ethanol.

18. A fuel composition of claim 1 wherein the acylating agent is predominantly or entirely an alkenylsuccinic acid or anhydride in which the alkenyl group has the formula

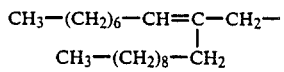

and wherein the alkanol polyamine consists essentially of 2-(2-aminoethylamino)ethanol.

19. A fuel composition of claim 1 wherein the acylating agent is predominantly or entirely an alkenylsuccinic acid or anhydride in which the alkenyl group has the formula

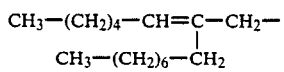

and wherein the alkanol polyamine consists essentially of 2-(2-aminoethylamino)ethanol.

20. A fuel composition of claim 1 wherein the acylating agent is an alkenyl-substituted succinic acid or anhydride and wherein the alkanol polyamine consists essentially of 2-(2-aminoethylamino)-ethanol.

21. A fuel composition of claim 5 wherein the alkanol polyamine consists essentially of 2-(2-aminoethylamino)ethanol.

22. A fuel composition for a spark-ignition internal combustion engine, which composition comprises:
(i) a major amount of a gasoline; and
(ii) a minor amount of a hydrocarbon-soluble detergent present in an amount sufficient to reduce the formation of carburetor deposits, the detergent being prepared by the process consisting essentially of reacting
(a) at least one hydrocarbon-substituted succinic acid or anhydride acylating agent containing an average of from about 16 to about 50 carbon atoms in the molecule and having an acyclic aliphatic substituent containing an average of at least 12 but less than 30 carbon atoms, with
(b) at least one alkanol polyamine containing an average of from 4 to 20 carbon atoms.

23. A fuel composition of claim 22 wherein the acyclic aliphatic substituent of the acylating agent is predominantly or entirely an alkyl or alkenyl group containing an average in the range of from about 18 to about 24 carbon atoms.

24. A fuel composition of claim 22 wherein the acylating agent is predominantly or entirely octadecenylsuccinic acid or anhydride.

25. A fuel composition of claim 22 wherein the alkanol polyamine is predominantly or entirely 2-(2-aminoethylamino)ethanol.

26. A fuel composition of claim 22 wherein the acyclic aliphatic substituent of the acylating agent is predominantly or entirely an alkyl or alkenyl group containing an average in the range of about 18 to about 24 carbon atoms, and wherein the alkanol polyamine consists essentially of 2-(2-aminoethylamino)ethanol.

27. A fuel composition of claim 22 wherein the acylating agent consists essentially of octadecenylsuccinic acid or anhydride and wherein the alkanol polyamine consists essentially of 2-(2-aminoethylamino)ethanol.

28. A fuel composition of claim 23 wherein the acylating agent consists essentially of hexadecenylsuccinic acid or anhydride and wherein the alkanol polyamine consists essentially of 2-(2-aminoethylamino-ethanol.

29. A fuel composition of claim 22 wherein the acylating agent consists essentially of a mixture of $C_{16}$, $C_{18}$, $C_{20}$, $C_{22}$, $C_{24}$, and $C_{26}$ alkenylsuccinic acids or anhydrides and wherein the alkanol polyamine consists essentially of 2-(2aminoethylamino)ethanol.

30. A fuel composition of claim 22 wherein the acylating agent is at least one succinic acid or anhydride and wherein the acyclic aliphatic group of such acylating agent is a substantially straight chain acyclic aliphatic group.

31. A fuel composition of claim 22 wherein the acylating agent is bifurcated on its beta carbon atom into two branches, one of which contains at least 4 carbon atoms and the other of which contains at least 6 carbon atoms.

32. A fuel composition of claim 22 wherein the acylating agent consists essentially of alkenyl-substituted succinic acid or anhydride in which the alkenyl group has the formula

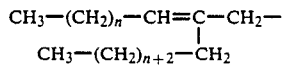

wherein n is an integer in the range of 2 to 10, and wherein the alkanol polyamine consists essentially of 2-(2-aminoethylamino)-ethanol.

33. A fuel composition of claim 32 wherein n is in the range of 4 to 10.

34. A fuel composition of claim 22 wherein the acylating agent consists essentially of alkenyl-substituted succinic acid or anhydride in which the alkenyl group has the formula

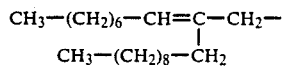

and wherein the alkanol polyamine consists essentially of 2-(2-aminoethylamino)ethanol.

35. A method for reducing deposits in a spark-ignited internal combustion engine, which method comprises:
(i) blending with a major amount of a liquid hydrocarbon fuel of the gasoline boiling range, a minor amount of a hydrocarbon-soluble detergent sufficient to reduce the formation of carburetor or injector deposits, the detergent being prepared by the process consisting essentially of reacting
(a) at least one aliphatic hydrocarbon-substituted succinic acid or anhydride acylating agent containing an average of from about 12 to about 50 carbon atoms in the molecule and having an acyclic aliphatic group containing an average of at least 12 but less than 30 carbon atoms; with (b) at least one alkanol polyamine containing an average of at least 4 carbon atoms; and (ii) using the resultant fuel composition to operate an internal combustion engine.

36. The method of claim 35 wherein the acylating agent is at least one hydrocarbon-substituted succinic acid or anhydride in which the hydrocarbon substituent contains an average of at least 16 but less than 30 carbon atoms, and wherein the alkanol polyamine contains an average of from 4 to 20 carbon atoms.

37. The method of claim 35 wherein the acylating agent consists essentially of at least one alkenyl succinic anhydride.

38. The method of claim 35 wherein the acylating agent consists essentially of octadecenylsuccinic acid or anhydride and wherein the alkanol polyamine consists essentially of 2-(2-aminoethylamino)ethanol.

* * * * *

UNITED STATES PATENT AND TRADEMARK OFFICE
CERTIFICATE OF CORRECTION

PATENT NO. : 4,997,456

DATED : March 5, 1991

INVENTOR(S) : Dennis J. Malfer

It is certified that error appears in the above-indentified patent and that said Letters Patent is hereby corrected as shown below:

On the title page, item [56] References Cited, under "U.S. PATENT DOCUMENTS" second column should read as follows:

| | | | |
|---|---|---|---|
| --4,240,803 | 12/1980 | Andress, Jr. | 44/63 |
| 4,329,249 | 5/1982 | Forsberg | 252/34.7 |
| 4,368,133 | 1/1983 | Forsberg | 252/75 |
| 4,435,297 | 3/1984 | Forsberg | 252/34.7 |
| 4,447,348 | 5/1984 | Forsberg | 252/75 |
| 4,448,703 | 5/1984 | Forsberg | 252/75 |
| 4,652,273 | 3/1987 | Maldonado et al. | 44/63 |
| 4,780,111 | 10/1988 | Dorer et al. | 44/63 |
| 4,863,487 | 9/1989 | Meyer et al. | 44/63 |
| 4,895,578 | 1/1990 | Meyer et al. | 44/63--. |

Column 2, line 34, reads "ar" and should read --are--.

UNITED STATES PATENT AND TRADEMARK OFFICE
CERTIFICATE OF CORRECTION

PATENT NO. : 4,997,456
DATED : March 5, 1991
INVENTOR(S) : Dennis J. Malfer

It is certified that error appears in the above-indentified patent and that said Letters Patent is hereby corrected as shown below:

Column 4, between lines 6 and 14, reads

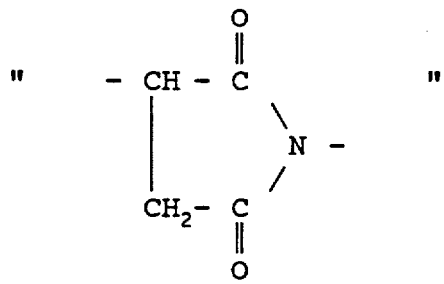

and should read

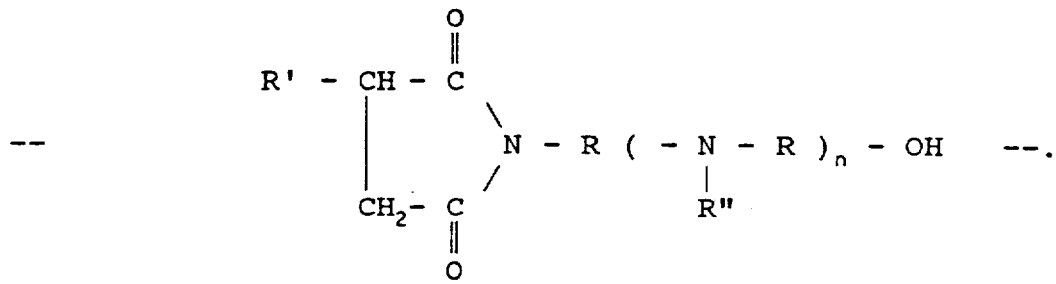

UNITED STATES PATENT AND TRADEMARK OFFICE
CERTIFICATE OF CORRECTION

PATENT NO. : 4,997,456
DATED : March 5, 1991
INVENTOR(S) : Dennis J. Malfer

It is certified that error appears in the above-indentified patent and that said Letters Patent is hereby corrected as shown below:

Column 4, between lines 24 and 32, reads

"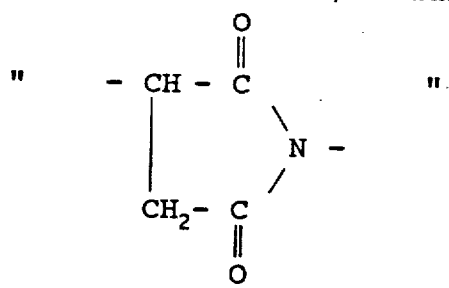".

and should read

--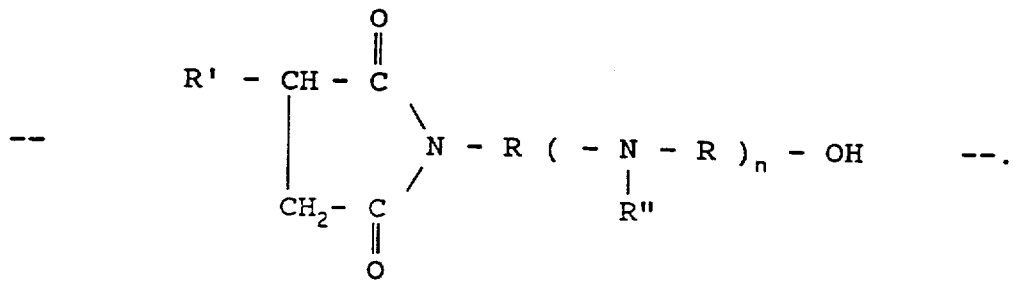--.

UNITED STATES PATENT AND TRADEMARK OFFICE
CERTIFICATE OF CORRECTION

PATENT NO. : 4,997,456
DATED : March 5, 1991
INVENTOR(S) : Dennis J. Malfer

It is certified that error appears in the above-indentified patent and that said Letters Patent is hereby corrected as shown below:

Column 9, lines 58-59, reads "nitric acid, or a polycarboxylic" and should read --nitric acid, or a similar oxidizing agent. Another method for preparing such polycarboxylic--.

Column 14, between lines 1 and 9,

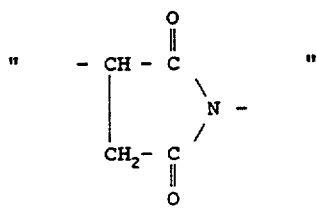

and should read

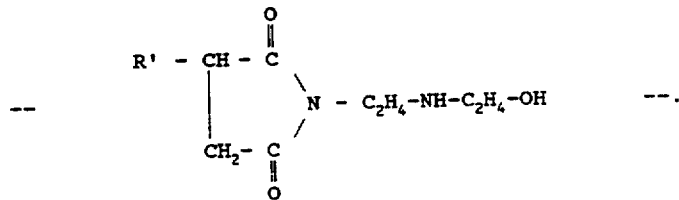

UNITED STATES PATENT AND TRADEMARK OFFICE
CERTIFICATE OF CORRECTION

Page 5 of 7

PATENT NO. : 4,997,456
DATED : March 5, 1991
INVENTOR(S) : Dennis J. Malfer

It is certified that error appears in the above-indentified patent and that said Letters Patent is hereby corrected as shown below:

Column 14, between lines 43 and 51, reads

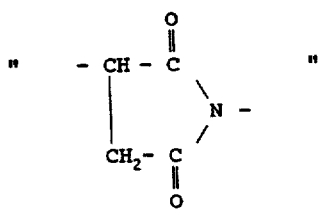

and should read

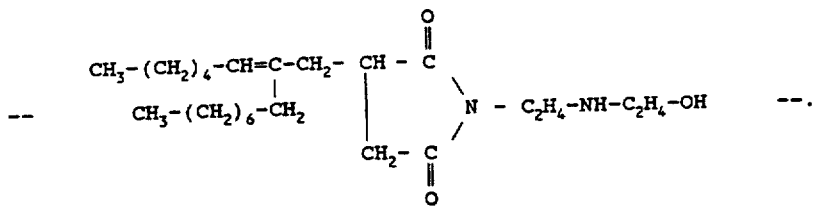

UNITED STATES PATENT AND TRADEMARK OFFICE
CERTIFICATE OF CORRECTION

PATENT NO. : 4,997,456
DATED : March 5, 1991
INVENTOR(S) : Dennis J. Malfer

It is certified that error appears in the above-indentified patent and that said Letters Patent is hereby corrected as shown below:

Column 15, between lines 1 and 9, reads

"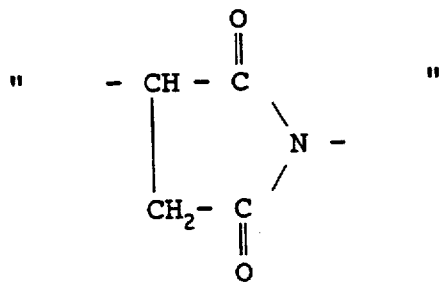"

and should read

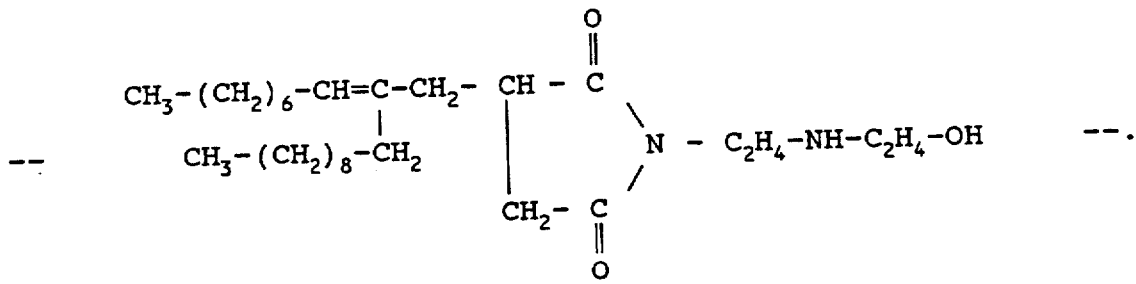

UNITED STATES PATENT AND TRADEMARK OFFICE
CERTIFICATE OF CORRECTION

PATENT NO. : 4,997,456
DATED : March 5, 1991
INVENTOR(S) : Dennis J. Malfer

It is certified that error appears in the above-indentified patent and that said Letters Patent is hereby corrected as shown below:

Column 15, line 23, reads "2-(2-aminoethylamine)ethanol" and should read --2-(2-aminoethylamino)ethanol--.

Column 16, line 67, reads "are at to provide" and should read --are at least sufficiently soluble in the hydrocarbon fuel being employed to provide--.

Column 17, line 18, reads "methylcyclopentadienylmanganes" and should read --methylcyclopentadienylmanganese--.

Column 17, line 66, reads "of claim wherein" and should read --of claim 1 wherein--.

Column 20, line 11, reads "claim 23" and should read --claim 22--.

Column 20, line 14, reads "2-(2-aminoethylamino-ethanol." and should read --2-(2-aminoethylamino)ethanol).--.

Column 20, line 20, reads "2-(2aminoethylamino)ethanol." and should read --2-(2-aminoethylamino)ethanol.--.

Signed and Sealed this

First Day of November, 1994

Attest:

BRUCE LEHMAN

Attesting Officer

Commissioner of Patents and Trademarks